United States Patent [19] [11] 3,954,736
Petri [45] May 4, 1976

[54] PRODUCTION OF LACTAMS
[75] Inventor: Norbert Petri, Ludwigshafen, Germany
[73] Assignee: BASF Aktiengesellschaft, Ludwigshafen (Rhine), Germany
[22] Filed: Oct. 27, 1970
[21] Appl. No.: 84,546

[30] Foreign Application Priority Data
Nov. 5, 1969  Germany.................... 1955559

[52] U.S. Cl..................... 260/239.3 A; 260/293.86
[51] Int. Cl.²..................................... C07D 201/04
[58] Field of Search............... 260/239.3 A; 23/1 F, 23/288 S, 288; 208/48 R

[56] References Cited

UNITED STATES PATENTS

| 2,670,193 | 2/1954 | Pyzel | 23/1 F |
| 2,706,704 | 4/1955 | Squires | 23/288 S |
| 3,210,338 | 10/1965 | Huber et al. | 260/239.3 A |

Primary Examiner—Henry R. Jiles
Assistant Examiner—Robert T. Bond
Attorney, Agent, or Firm—Johnston, Keil, Thompson & Shurtleff

[57] ABSTRACT

Continuous production of lactams by rearrangement of cycloalkanone oximes at from 210° to 450°C in contact with a supported catalyst in a fluidized bed wherein from 0.01 to 1 kg of steam is introduced above the fluidized bed for each kg of cycloalkanone oxime supplied. Lactams are starting materials for the production of synthetic polyamides suitable for fibers.

9 Claims, No Drawings

PRODUCTION OF LACTAMS

The invention relates to the continuous production of lactams by rearrangement of cycloalkanone oximes in the gas phase and particularly to a method of avoiding disturbances.

The catalytic rearrangement of oximes of cyclic ketones into lactams at elevated temperature in contact with a catalyst consisting mainly of boron oxide and a carrier is known. The process is preferably carried out using a fluidized catalyst. It has been found that disturbances often arise in this process because a mixture of boric acid volatilized from the catalyst and lactam condense from the vapor phase above the fluidized bed on the cooler walls of the reactor and the discharge pipes from the reactor, for example on the walls of the discharge pipe for the vapor mixture leaving the reactor, and forms, with the entrained catalyst dust, agglomerates with either result in stoppages or, if they drop off from the reactor walls, fall back into the fluidized bed and cause disturbances therein.

It is an object of the invention to provide an improved process for the production of lactams by catalytic rearrangement of cycloalkanone oximes which avoids condensation of solid material in the pipe system for the reaction gases leaving the reactor.

It is another object of the invention to provide an improved process for the continuous production of lactams by catalytic rearrangement of cycloalkanone oximes which avoids disturbances by solid material primarily condensed in the upper part of the reactor and falling into the fluidized bed.

These and other objects and advantages will be better understood from the following detailed description.

I have found that lactams can be prepared continuously by rearrangement of cycloalkanone oximes at from 210° to 450°C in contact with a supported catalyst in a fluidized bed while avoiding the said disadvantages by introducing steam above the fluidized bed, preferably in a superheated condition, into the reactor at the rate of 0.01 to 1 kg of steam per kg of cycloalkanone oxime introduced.

The conditions in the rearrangement of oximes of cyclic ketones are known. The method is suitable for example for cycloalkanone oximes having five to twelve carbon atoms such as cyclopentanone oxime, cyclohexanone oxime, methylhexanone oxime, cyclooctanone oxime and cyclododecanone oxime. It has special importance for the rearrangement of cyclohexanone oxime. The cycloalkanone oxime is introduced into the fluidized bed either as a vapor, a liquid or a solid, the catalyst in the fluidized bed being kept at the reaction temperature. The rearrangement is carried out at from 210° to 450°C, preferably from 270° to 370°C. The process may be carried out at atmospheric, subatmospheric or slightly elevated pressure. When the process is carried out at subatmospheric pressure, the pressure range of from 20 to 200 mm is preferred. When the process is carried out at superatmospheric pressure, pressures of more than 2 atmospheres are not generally used. The process may be carried out in the presence of an inert gas, for example carbon dioxide, argon, nitrogen, ethane or steam. The inert gas is often utilized to keep the catalyst fluidized. It is also advantageous to use as starting material a cycloalkanone which has a certain water content, for example from 1 to 10% by weight, resulting from its manufacture. The inert gas is generally added in an amount of from 5 to 80% by volume with reference to the gas mixture, depending on whether the process is carried out at atmospheric or superatmospheric pressure or at subatmospheric pressure, more inert gas being used at the higher pressures. If steam is used as the inert gas, it is advantageous to use smaller amounts of the same, for example up to 10% by volume, because otherwise the boric acid applied to the supported catalyst volatilizes too much.

Known catalysts are used in which boron oxide or boric acid is present on a carrier, particularly aluminum oxide in its various modifications such as alumina, γ-aluminum oxide or boehmite, or on silicic acid or on titanium oxide or mixtures of such oxides or of compounds of the oxides with each other, for example aluminum silicates. The ratio by weight of boron oxide (or boric acid calculated as boron oxide) to carrier is generally from 1:9 to 1:1. In the preferred catalysts the amount of boron oxide is from 25 to 50% by weight. The catalysts may also be modified by additives, for example manganese salts, cobalt salts or nickel salts in an amount of up to 10% by weight. The catalysts are prepared by conventional methods, for example the carrier may be impregnated with boric acid or ammonium borate solution, dired at from 50° to 200°C and then calcined at from 600° to 850°C. The catalysts are shaped by conventional methods, for example by making the catalyst and carrier into a paste with a little water, mixing in a kneader, pressing the mixture into pellets or tablets, drying and calcining at the said temperature. Particle sizes of from 0.005 to 1.5 mm, particularly from 0.2 to 1.0 mm, are conveniently used for the fluidized catalysts. The height of the bed of catalyst is advantageously chosen so that the residence time of the oxime in the catalyst bed is from 0.01 to 20 seconds, preferably from 0.1 to 3 seconds.

In accordance with the invention, steam is injected above the fluidized bed, i.e. in a region from about 200 mm above the fluidized bed to the cover of the reactor which is usually more than 4000 mm up to 6000 mm above the fluidized bed. The steam generally has a temperature of from 160° to 450°C, this temperature being advantageously from 50° to 100°C below the rearrangement temperature. Superheated steam is preferably used. The amount of steam is from 0.01 to 1 kg per kg of cycloalkanone oxime used. The steam may be supplied radially or tangentially and the direction may be perpendicular to or inclined upwardly or downwardly to the perpendicular to the vertical axis of the fluidization reactor. It is sufficient to supply the steam at one point, but it may be supplied at more than one point at the same level or at different levels. When steam is fed in above the fluidized bed in accordance with the invention, the reactor may be operated for weeks on an industrial scale without encrustation or agglomeration on the walls above the fluidized bed in the reactor, and the pipelines leading from the reactor remain unobstructed. This result is surprising because supplying appropriate amount of steam with the cycloalkanone oxime through the catalyst cannot prevent such encrustation or agglomeration.

When steam is not added above the fluidized bed however, particularly the discharge pipe for the vapor leaving the reactor is constricted to such an extent by encrustation on its wall after a short time that an undesirable rise in pressure takes place in the reactor. Moreover there are disturbances in the fluidized bed, particularly by crusts detached from the walls of the reactor.

The following Examples illustrate the invention.

EXAMPLE 1

A fluidized bed having a height of 1000 mm and consisting of 180 kg of a catalyst which consists of 51% by weight of $Al_2O_3$ and 49% by weight of $B_2O_3$ having a particle size of from 0.2 to 1 mm and a bulk density of 0.5 kg per liter is situated in a fluidization reactor having a height of 2000 mm and a diameter of 678 mm. The fluidized bed is kept fluidized by supplying 120 m³ (STP) per hour of nitrogen. 200 kg per hour of cyclohexanone oxime having a water content of 5% is introduced as a liquid directly into the catalyst bed which is heated to 360°C and thus rearranged into caprolactam. 25 kg per hour of steam at a temperature of 280°C is passed into the reactor 700 mm above the fluidized bed through a pipe having a diameter of 25 mm. The reactor and the discharge pipe for the vapor mixture leaving the reactor remain free from encrustation during operation extending over 5 months.

EXAMPLE 2

240 kg per hour of a cyclohexanone oxime melt having a water content of 4% is injected through a nozzle into the catalyst bed described in Example 1 at 350°C and a pressure of 830 mm in the fluidization reactor described in Example 1. 300 mm above the fluidized bed a total of 40 kg per hour of steam at a temperature of 310°C is introduced through three tubes arranged tangentially around the periphery of the reactor. No encrustation of the upper portion of the reactor or of the reactor outlets is observed after 261 hours operation.

EXAMPLE 3

Using the fluidization reactor described in Example 1, 180 kg per hour of finely divided cyclohexanone oxime having a water content of 6% is introduced with nitrogen, at a pressure within the reactor of 805 mm, into the fluidized bed which is at a temperature of 355°C and which is formed by 100 kg per hour of a catalyst in the form of chips having a particle size of 0.3 to 0.8 mm and consisting of 15% of $B_2O_3$, 84% of $TiO_2$ and 0.8% of $H_2O$, the catalyst being fluidized with 130 m³ (STP) per hour of nitrogen. 18 kg per hour of steam at 250°C is introduced at the height of the outlet from the fluidization reactor, i.e. 1000 mm above the fluidized bed. The outlet from the reactor and the attached pipes are kept free from agglomerates in this way.

EXAMPLE 4

150 kg/hour of liquid cyclooctanone oxime having a water content of 0.06% is injected into the fluidized bed of catalyst heated to 300°C in the fluidization reactor described in Example 1. 180 kg per hour of catalyst (consisting of an aluminum oxide in the form of chips having a particle size of from 0.3 to 0.5 mm which has been calcined at 800°C and having a content of 50% of $B_2O_3$) is fluidized with 120 m³ (STP) per hour. 20 kg per hour of steam at 230°C is introduced through a pipe situated 600 mm above the fluidized bed. The upper part of the reactor and the reactor outlet remain devoid of obstructions.

EXAMPLE 5

7.3 kg per hour of cyclohexanone oxime having a water content of 6% is rearranged at 360°C and a pressure of 280 mm in contact with 4.0 kg per hour of catalyst in a fluidization reactor having a length of 2000 mm and a diameter of 100 mm to form caprolactam. The catalyst consists of aluminum oxide with 45% of boron oxide and has a particle size of from 0.2 to 0.5 mm. The fluidized bed is maintained by 1.1 m³ (STP) per hour of nitrogen and the reaction vapor. 1 kg per hour of steam at 240°C is injected through the cover of the upper part of the reactor at an angle. No deposition takes place in the outlet from the reactor or in the attached pipes.

I claim:
1. An improved process for the production of lactams having from 5 to 12 ring carbon atoms by rearrangement of a corresponding cycloalkanone oxime at from 210° to 450°C in contact with a supported catalyst in a fluidized bed in a continuous process wherein the improvement consists in introducing steam at the rate of from 0.01 to 1 kg per kg of cycloalkanone oxime introduced, the steam being injected into the space above the fluidized bed.

2. A process as claimed in claim 1 wherein superheated steam is used.

3. A process as claimed in claim 1 wherein the cycloalkanone oxime used contains from 1 to 10% by weight of water.

4. A process as claimed in claim 1 wherein an inert gas is present.

5. A process as claimed in claim 1 wherein the residence time of the oxime in the fluidized bed is from 0.01 to 20 seconds.

6. A process as claimed in claim 1 wherein the steam is introduced at a point at least 200 mm above the fluidized bed.

7. A process as claimed in claim 1 wherein the same is introduced at a temperature of from 160° to 450°C which is from 50° to 100°C below the rearrangement temperature.

8. A process as claimed in claim 1, wherein said oxime is cycloalkanone oxime.

9. A process as claimed in claim 7, wherein steam is introduced at a point from 200 mm to 6000 mm above said fluidized bed.

* * * * *